US 11,596,395 B2

(12) United States Patent
Trombetta et al.

(10) Patent No.: US 11,596,395 B2
(45) Date of Patent: Mar. 7, 2023

(54) CUTTING DEVICE FOR SURGICAL THREADS

(71) Applicant: MEDACTA INTERNATIONAL SA, Castel San Pietro (CH)

(72) Inventors: Christian Trombetta, Castel San Pietro (CH); Massimiliano Bernardoni, Castel San Pietro (CH); Francesco Siccardi, Castel San Pietro (CH)

(73) Assignee: Medacta International SA, Castel San Pietro (CH)

( * ) Notice: Subject to any disclaimer, the term of this patent is extended or adjusted under 35 U.S.C. 154(b) by 117 days.

(21) Appl. No.: 17/263,013

(22) PCT Filed: Jul. 10, 2019

(86) PCT No.: PCT/IB2019/055872
§ 371 (c)(1),
(2) Date: Jan. 25, 2021

(87) PCT Pub. No.: WO2020/021371
PCT Pub. Date: Jan. 30, 2020

(65) Prior Publication Data
US 2021/0161521 A1    Jun. 3, 2021

(30) Foreign Application Priority Data

Jul. 26, 2018   (IT) .................. 102018000007518

(51) Int. Cl.
*A61B 17/04* (2006.01)
*A61B 90/00* (2016.01)
*A61B 17/00* (2006.01)

(52) U.S. Cl.
CPC *A61B 17/0467* (2013.01); *A61B 2017/00477* (2013.01); *A61B 2090/08021* (2016.02)

(58) Field of Classification Search
CPC .................. A61B 17/0467; A61B 2017/00477
See application file for complete search history.

(56) References Cited

U.S. PATENT DOCUMENTS 3,959,960 A * 6/1976 Santos ............... A61B 17/8861
57/22
3,995,619 A * 12/1976 Glatzer .............. A61B 10/0275
606/171

(Continued)

FOREIGN PATENT DOCUMENTS

WO     2017025971 A1     2/2017

OTHER PUBLICATIONS

International Search Report and Written Opinion for International Application No. PCT/IB2019/055872 dated Nov. 27, 2019.

*Primary Examiner* — Ryan J. Severson
(74) *Attorney, Agent, or Firm* — Meunier Carlin & Curfman LLC (57) ABSTRACT

A cutting device for surgical threads comprises a guide body that has an internal axial cavity and a first cutting area defined by an abutment surface; a cutting body that has a central portion that extends along a longitudinal axis and a second cutting area defined by an abutment surface, wherein the second cutting area abuts the second first cutting area when the cutting body is received in a housing portion of the guide body; and an actuator element capable of causing the cutting body to rotate relative to the guide body about the longitudinal axis between a first position, in which the first and second cutting areas, define a passageway that communicates with the internal axial cavity, and a second position, in which said passageway is at least partially obstructed by a counter-rotating movement of the abutment surfaces, which intersect tangentially so as to cut the surgical thread therebetween.

12 Claims, 10 Drawing Sheets

(56) References Cited

U.S. PATENT DOCUMENTS

| | | | | |
|---|---|---|---|---|
| 5,474,565 A * | 12/1995 | Trott | A61B 17/06109 | 606/139 |
| 5,549,623 A * | 8/1996 | Sharpe | A61B 17/3201 | 606/174 |
| 7,879,055 B1 * | 2/2011 | Stone | A61B 17/0467 | 606/170 |
| 7,918,867 B2 * | 4/2011 | Dana | A61B 17/0467 | 606/139 |
| 8,105,355 B2 * | 1/2012 | Page | A61B 17/0487 | 606/232 |
| 8,211,123 B2 * | 7/2012 | Gross | A61B 17/0485 | 606/167 |
| 8,252,005 B2 * | 8/2012 | Findlay, III | A61B 17/0467 | 606/139 |
| 8,282,659 B2 * | 10/2012 | Oren | A61B 17/0467 | 606/139 |
| 8,469,983 B2 * | 6/2013 | Fung | A61B 17/0467 | 606/170 |
| 8,480,691 B2 * | 7/2013 | Dana | A61B 17/0467 | 606/148 |
| 8,603,125 B2 * | 12/2013 | Stone | A61B 17/0469 | 606/148 |
| 8,834,497 B2 * | 9/2014 | Snell | A61B 17/0467 | 606/167 |
| 9,078,631 B2 * | 7/2015 | Tegels | A61B 17/0057 | |
| 9,247,935 B2 * | 2/2016 | George | A61B 17/0467 | |
| 9,681,866 B2 * | 6/2017 | Halac | A61B 17/0467 | |
| 10,426,462 B2 * | 10/2019 | Haberman | A61B 17/0469 | |
| 10,595,854 B2 * | 3/2020 | Nachmias | A61B 17/0467 | |
| 11,219,447 B2 * | 1/2022 | Juan | A61B 17/0467 | |
| 2003/0120287 A1 * | 6/2003 | Gross | A61B 17/0467 | 606/148 |
| 2003/0181926 A1 * | 9/2003 | Dana | A61B 17/0467 | 606/148 |
| 2005/0234481 A1 * | 10/2005 | Waller | A61B 17/0467 | 606/148 |
| 2007/0005081 A1 * | 1/2007 | Findlay, III | A61B 17/0487 | 606/148 |
| 2007/0106310 A1 * | 5/2007 | Goldin | A61B 17/0467 | 606/148 |
| 2007/0173865 A1 * | 7/2007 | Oren | A61B 17/0467 | 606/148 |
| 2008/0234729 A1 * | 9/2008 | Page | A61B 17/0485 | 606/232 |
| 2009/0082797 A1 | 3/2009 | Fung et al. | | |
| 2010/0069922 A1 * | 3/2010 | Kaufman | A61B 17/0467 | 606/138 |
| 2011/0029012 A1 * | 2/2011 | Tegels | A61B 17/0057 | 606/213 |
| 2011/0100173 A1 * | 5/2011 | Stone | A61B 17/0482 | 83/13 |
| 2011/0106104 A1 * | 5/2011 | Dana | G06F 17/16 | 606/148 |
| 2012/0136378 A1 * | 5/2012 | Snell | A61B 17/0467 | 606/148 |
| 2013/0079802 A1 | 3/2013 | Halac et al. | | |
| 2014/0005689 A1 * | 1/2014 | Griffiths | A61B 17/0467 | 606/138 |
| 2015/0088163 A1 * | 3/2015 | George | A61B 17/0467 | 606/138 |
| 2017/0042532 A1 * | 2/2017 | Valadez | A61B 17/0482 | |
| 2018/0228485 A1 * | 8/2018 | Haberman | A61B 17/0469 | |
| 2018/0235600 A1 * | 8/2018 | Nachmias | A61B 17/0467 | |
| 2019/0374215 A1 * | 12/2019 | Juan | A61B 17/0485 | |
| 2020/0390434 A1 * | 12/2020 | Fu | A61B 17/0467 | |
| 2021/0161521 A1 * | 6/2021 | Trombetta | A61B 17/0467 | |

\* cited by examiner

CUTTING DEVICE FOR SURGICAL THREADS

TECHNICAL FIELD

The present invention relates to a tool for cutting operating wires during surgery.

PRIOR ART

During surgery, it is known to use operating wires. Depending on the needs for which the surgical wires are used, they will have different structural characteristics, such as, for example, different degrees of rigidity, different materials, different diameters and so on.

A first example of surgical threads is suture threads, i.e. threads that are used to close wounds in or on the patient's body; a second example of surgical threads is cerclage wire, by means of which it is possible to join bone fragments that do not fit together.

Various devices are known for cutting the different types of surgical threads used by the surgeon during surgical operations. Each device is optimised to meet the cutting requirements imposed by the particular features of the threads used.

When it is necessary to use a surgical thread during surgery to join two or more parts of the patient's body structure, for example to close a wound in the patient's body or to join bone fragments, a surgical thread of the type appropriate to the operation in progress is used. In the typical case of closing a wound in the patient's body, the surgical thread is passed through the patient's soft tissue that surrounds the wound that needs closing, alternately on one side and then on the other. The suture thread is then stretched to bring the wound's edges closer together and everything is fixed by means of a special knot. It is known to occur that, following the tying of a knot, some lengths of wire remain outside it. It is, therefore, necessary to cut the ends of thread protruding outside the knot to avoid unintended and adverse effects thereof on the suture, causing detriment to the wound's complete healing.

In the case, on the other hand, in which a bone structure does not appear cohesive as the anatomy correctly requires, the incohesive parts may be joined to the main structure using a surgical wire, which is known in the state of the art as cerclage wire.

The use of cerclage wire is necessary, for example, when a femur fracture leads to a lack of cohesion of part of the femur bone with respect to the femoral bone structure. In this case, the surgeon binds the two parts of the femur with a metal wire, the cerclage wire, tightening them together, in order to facilitate bone regeneration and the setting of two bone fragments, thus healing the fracture. Once the two portions of the bone have been placed as needed, the surgeon joins the two ends of cerclage wire, for example in a knot. As described above in relation to suture threads, and as is known from common experience, the knot tied thus has wire ends protruding from the knot that must be removed.

The prior art involves the surgeon's using cutting tools for this purpose, such as, for example, wire cutters. These tools are inserted into the patient's body, as close as possible to the knot, and then the wire ends protruding from the knot are cut.

To cut suture threads, on the other hand, surgical scissors, that are shaped so as to come as close to the patient's tissue as possible, are used in order to minimise the amount of thread that remains protruding from the knot.

According to the rules of minimally invasive surgery, there is a tendency to make the smallest possible incisions in the patient during these surgical operations in order to speed up recovery. It is therefore clear that the size of the surgical tools must be kept to a minimum, while ensuring, at the same time, that the surgeon can operate safely inside the patient's body.

It is immediately intelligible to the person skilled in the art, therefore, that the classic shape of the known tools indicated above has drawbacks that the present invention is intended to solve. In fact, the structure of the common tools is based on two blades that are hinged together in a fulcrum and are capable of moving towards and away from each other when thus controlled by means of handgrips. To cut a thread using these known means, it is necessary to gather the thread between the blades, which must not, therefore, be in contact with each other; in other words, there must be a space between the two blades in which to house the thread before cutting. This increases the overall size of the cutting tool when it is not in the configuration for use. In addition, the common tools require that the blades have a significant characteristic size so as to provide a cutting surface large enough to allow the surgeon a smooth cut. This is especially true in conditions of poor visibility, such as those of a surgical site, where blood and other body fluids can limit the surgeon's operational visibility. As well as placing the surgeon at risk of damaging the tissue during the known cutting device's installation step, limited visibility also helps to increase the risk for the surgeon of damaging the tissue during the cutting step and those steps immediately following the cutting step, as well as during the step of removing the tool from the patient's body.

Another drawback of the state of the art is the presence of sharp objects near the patient's tissue, which requires the surgeon to operate with the utmost care in order not to damage the surrounding tissue. This increases the time needed for surgical operations and the related stress for the surgeon.

Another drawback is the choice of the blades' position inside the surgical site. This operation, in fact, involves identifying the position of the knot inside the patient's body, where body fluids often reduce visibility. Due to this reduced visibility, it is often necessary to proceed with the aid of touch in order to correctly position the blades.

The purpose of the present invention is to present a cutting device for surgical threads that overcomes the drawbacks of the prior art described above.

One of the purposes of the present invention is, in fact, to provide a cutting device for surgical threads that is minimally invasive, and that guarantees the patient a completely safe cut without any damage to the surrounding soft tissue.

In addition, the purpose of the present invention is to provide a cutting device for a surgical thread that is easy for the surgeon to use and that allows a quick and safe cut despite the fact that the surgical site does not allow the surgeon good visibility.

These and other purposes are broadly attained by a cutting device for surgical thread, and by a cutting method for a surgical thread with said device, as described in one or more of the appended claims.

Additional characteristics and benefits will be more apparent from the detailed description of a preferred, but not exclusive, embodiment of a cutting device for surgical threads, according to the present invention.

Additional advantageous characteristics are set out in the dependent claims.

BRIEF DESCRIPTION OF THE DRAWINGS

The present invention will now be described in greater detail, with reference to the accompanying drawings provided merely by way of example, in which.

DETAILED DESCRIPTION

In the above Figures, the number 100 designates in its entirety a cutting device for surgical threads, according to the present invention.

In the example shown, the apparatus 100 is suitable for use during surgery in which a surgical thread of any kind is used, such as a suture thread, a cerclage wire, or the like.

In the present description, the terms "proximal" and "distal" will be used with reference to the position of the element relative to the patient.

The cutting device for surgical threads comprises a guide body 120 that has a tubular-shaped housing portion 121, extending along a longitudinal axis 120a, and equipped, internally, with an axial cavity 129, adapted to receive a surgical thread.

The guide body 120, and, in particular, the housing portion 121, comprises a first end 120' that is at least partially open, to allow the insertion of the surgical thread, and a second end 120", axially opposite to the first 120', which is also open.

More specifically, the housing portion 121 has a cylindrical shape with a through axial cavity 129 extending along the entire longitudinal extension of the housing portion 121, and having at the ends 120' and 120" respective openings 124 and 130 that are capable of placing the axial cavity 129 in fluid communication with the external environment.

As already stated, the terms "proximal" and "distal" are used, in the present description, with reference to the position of the element with respect to the patient.

On the basis of this, it is possible to define the opening 124 as the proximal opening and the opening 130 as the distal opening.

It is possible, therefore, to identify a main direction of extension Y, along which the housing portion 121 develops.

The guide body 120 has a first cutting area 122 defined by an abutment surface 122' oriented parallel to the longitudinal extension axis 120a of the housing portion 121.

Specifically, the first cutting area 122 of the guide body 120 has a substantially semi-cylindrical shape with its base 122a transverse to the longitudinal axis 120a of the housing portion 121; the abutment surface 122' extends partially within the axial cavity 129 and takes the shape of a shoulder that partly obstructs the proximal opening 124.

This configuration allows the creation of an area suitable for accommodating the knot of the surgical thread and distancing the cutting area from the soft tissue of the surgical site, to prevent the soft tissue from interfering with the cutting area.

In a preferred embodiment, the first cutting area is large enough to obstruct about half of the distal opening 124. In other words, the abutment surface 122' is flat or, alternatively, has two faces inclined towards each other to form an angle between 150° and 170°. This first cutting area does not have a genuine blade but a sharp edge at the limit of the abutment surface 122' inside the axial cavity 129. The cutting device 100, the subject of the present invention, also comprises a cutting body 230 comprising an elongated central portion 231, which extends along a main direction of extension X along a longitudinal axis 230a. The central portion 231 of the cutting body 230 is suitable for insertion into the housing portion 121 of the guide body 120.

The central portion 231 has a cross-section at the longitudinal axis 230a so that, when coupled and inserted inside the axial cavity 129 of the housing portion 121, it defines a passage channel 300, extending parallel to the longitudinal axis 120a, for the housing of the surgical thread.

The cutting body 230 comprises a first end 230' equipped with a second cutting area 232 defined by an abutment surface 232', oriented parallel to the longitudinal extension axis 230a of the cutting body 230.

The cutting body 230 also has a second end 230", axially opposite the first 230', with an opening 237 for the exit of the surgical thread.

The central portion 231 can have a cross-section with various geometrical arrangements: planar, cross, semi-circular, circular sector, or any other geometric shape that does not have a completely circular cross-section because it must define, as mentioned above, an abutment surface 232' extending parallel to the longitudinal extension axis 230a, which can interact with the abutment surface 122' of the guide body 120 to be able to cut the surgical thread, as explained below.

The outer edge of the abutment surface 232', placed near the first end 230', may be sharp or have a cutting edge, even if not sharp, but which, by interfering with the cutting edge of the abutment surface 122', causes the cutting of the surgical thread that is found between the two surfaces.

In a preferred embodiment, shown here purely by way of example, the cutting body 230 has a cross-section that is preferably semi-circular, with a non-planar abutment surface 232', with two sides inclined towards each other to form an angle between 150° and 180° (exclusive), preferably between 150° and 170°. In other words, the central portion 231 has an elongated shape with a section that takes the form of a circular sector the angle of which is greater than 90 degrees: the central portion 231 has a surface 240 shaped like a depression or a V. In this way, the surgical thread, when inserted inside the passage channel 300, is received in this surface depression 240, so as to be stably guided inside the cutting device 100 and to remain still during the cutting operation. If the cutting body 230 is at least partially received in the housing portion 121, the second cutting area 232 abuts against the first cutting area 122.

Figure 9:
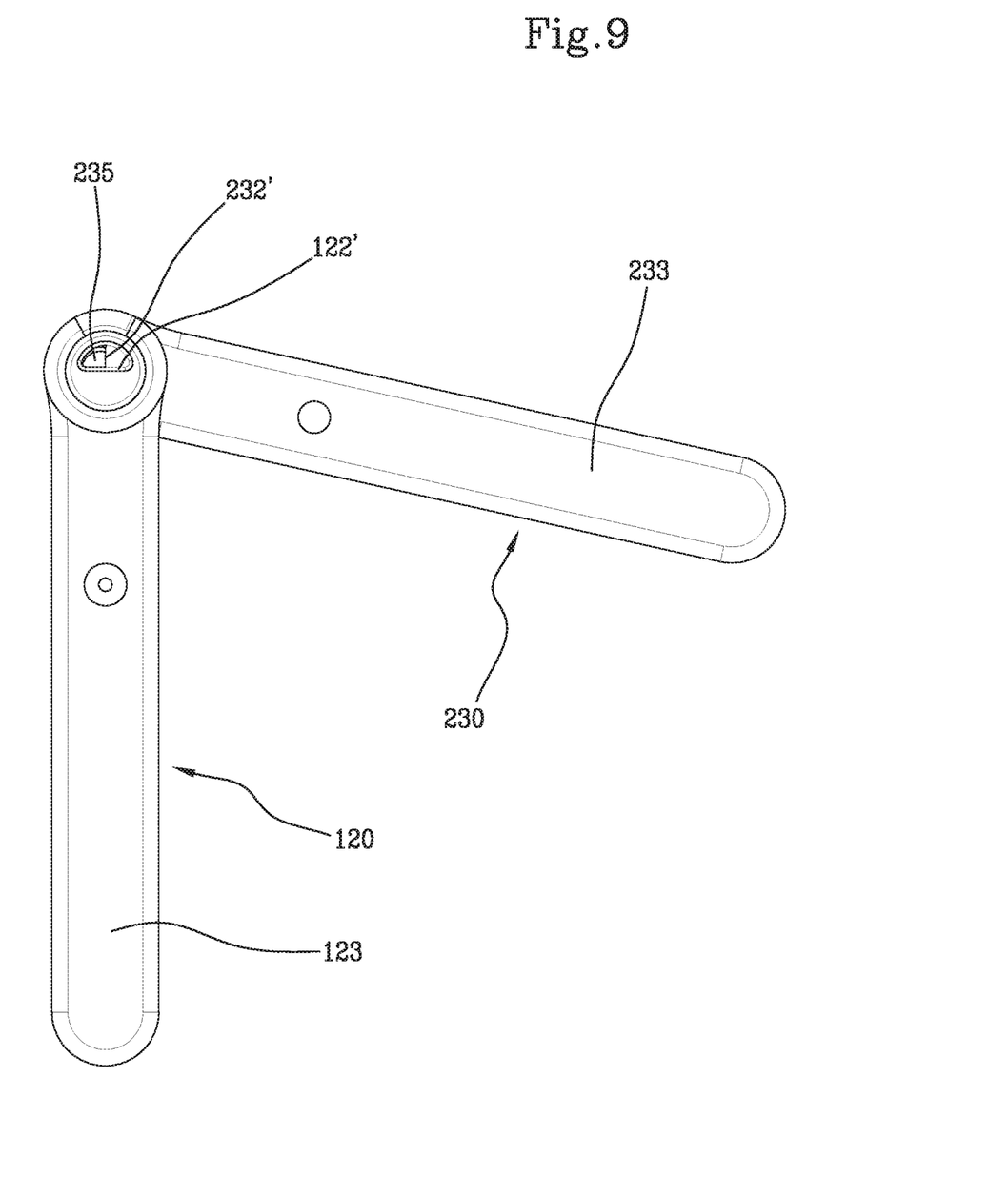
FIG. 9 shows an operating step in which the cutting device is used.

The cutting device 100 also comprises an actuator element 233, capable of causing the cutting body 230 to rotate relative to the guide body 120 around the longitudinal extension axis 230a between a first position in which the abutment surfaces 122', 232' of the first cutting area 122 and of the second cutting area 232 respectively are arranged relative to each other so as to identify a passageway 235 (FIG. 10), communicating with the internal axial cavity 129, at the first ends 120', 230' of the guide body 120 and of the cutting body 230 respectively, and a second position in which the passageway 235 is at least partially obstructed (FIG. 9) by the counter-rotating movement of the abutment surfaces 122', 232' that intersect/cross tangentially to cut the surgical thread inserted between them.

Advantageously, the actuator element 233 is connected to the cutting body 230 preferably at the second end 230" of the cutting portion 230.

In an illustrated embodiment, the actuator element 233 is elongated in radial extension from the distal end 230" of the cutting portion 230.

The cutting device 100 for surgical wires, and in particular the guide body 120, has a gripping area 123 to allow the device to be held during operations.

The gripping area 123 is angled with respect to the central axis 120a of the housing portion 121 and connected to it, to allow an easy grip of the cutting device 100. The preferred angle of the gripping area 123 to the axis 120a is between 30 and 120 degrees or, more precisely, about 90 degrees. Different angles of said gripping area 123 are not to be regarded as excluded from the scope of the present invention.

As mentioned, the gripping area 123 is connected to the guide body 120. Said connection is preferably made near the opening 130 placed at the second end 120" of the housing area 121. Other positions may also be possible, such as along the axial extension of the guide body 120.

When using the cutting device 100, the gripping area 123 is the part of the cutting device 100 that is distal from the patient, while the opening 124 is in a proximal position to the patient's body, at the first end 120'.

The guide body 120 has a coupling area 125 suitable for coupling the guide body 120 to the cutting body 230.

This coupling area 125 is advantageously located in a distal position with respect to the patient, i.e. at the second ends 120" and 230" respectively of the guide body 120 and of the cutting body 230.

The coupling area 125 comprises a bushing 131 with a circular section that is preferably larger than the diameter of the housing portion 121. This bushing 131 is preferably positioned at the connection area between the gripping area 123 and the central portion 231 of the cutting portion 230.

The coupling area 125 also has a radial projection 236, protruding from the aforementioned bushing 131, provided at the second end 230" of the cutting area 230. The projection 236 is radial with respect to the longitudinal extension axis 230a of the central portion 231.

The coupling area 125 also comprises a groove 126, in the form of a radial annular furrow provided at the second end 120" of the guide body 120. This groove 126 is adapted to receive the aforementioned projection 236, so as to allow mutual engagement, correct and stable relative axial positioning, and relative rotation between the cutting body 230 and the guide body 120.

The coupling area 125 embraces the distal end of the guide body 120, housing the proximal opening 130 internally.

In addition, the coupling area 125 has, on the guide body 120, a notch 128 that interrupts the groove 126 allowing access to the projection 236 to that groove 126 from the outside.

Advantageously, the notch 128 is made in a position diametrically opposed to the one from which the gripping area 123 begins.

The coupling between the guide body 120 and the cutting body 230 takes place by inserting the central portion 231 into the housing portion 121, axially aligning the projection 236 at the notch 128, inserting it into the latter, so as to bring the second cutting area 232 to abut against the first cutting area 122.

In this way too, the projection 236 is radially aligned with the groove 126. By rotating the cutting body 230 with respect to the guide body 120, the projection 236 is inserted and slid into the groove 126, thus blocking the relative axial movement between the cutting body 230 and the guide body 120.

Along the gripping area 123 of the guide body 120, and preferably located on its distal surface, there is a locking element 127; the actuator element 233 has, instead, a cavity 234 adapted to receive the aforementioned locking element 127 inside it.

This locking element 127 has, advantageously, a sphere 140 housed inside a recess 141 and protruding from it. Between the lower wall of the recess 141 and sphere 140 there is an elastic element (not shown) that acts as an elastic abutment, for example as a spring.

Figure 10:
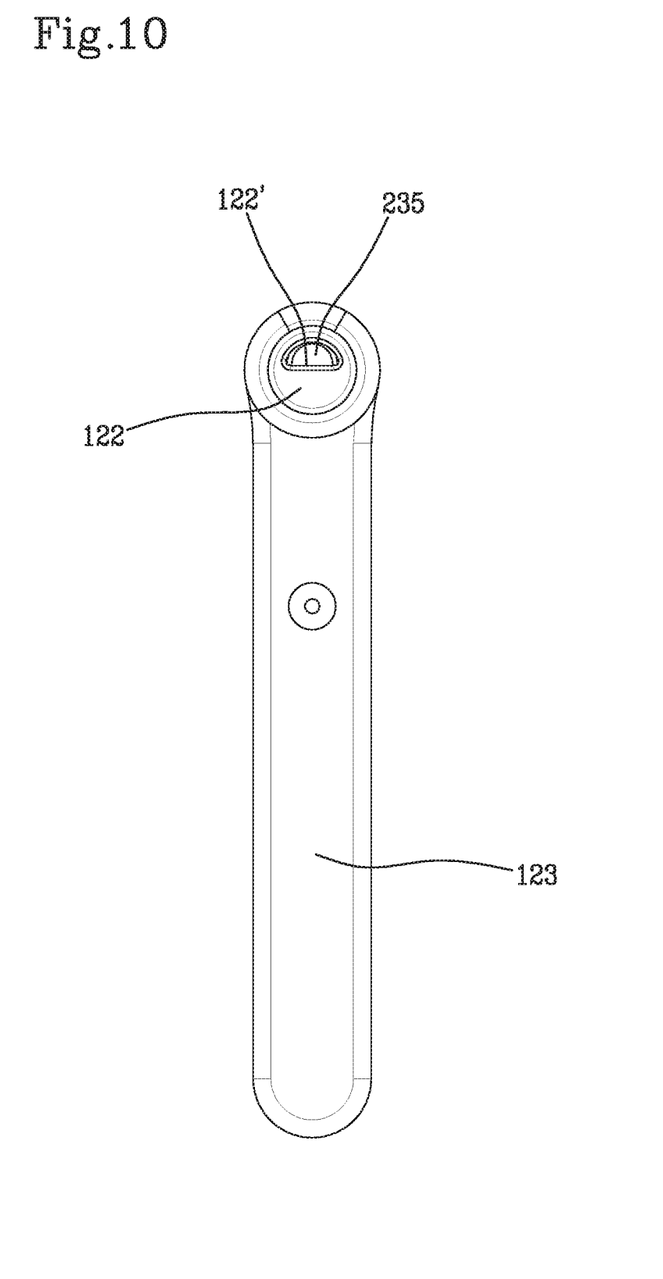
FIG. 10 shows a first operating position.

Following the insertion of the central portion 231 into the housing portion 121, and the relative rotation of the cutting body 230 with respect to the guide body 120 around the longitudinal axis 230a, the actuator element 233 and the handgrip 123 rotate relatively with respect to each other from an initial engagement position, in which they are aligned and oriented in diametrically opposite directions to the longitudinal axis 230a (FIG. 8), to an operating position, in which they are aligned, superimposed and oriented in the same direction with respect to the longitudinal extension axis 230a (FIG. 10).

In this last operating position, the locking element 127 is engaged in the cavity 234, forcing the guide portion 120 and the cutting portion 230 into the first position. Once the device has been assembled, the surgical thread can be cut.

At the end of the assembly operation, the excess portion of surgical thread is inserted, which must be removed inside the axial cavity 129 of the guide body 120 through the opening 124 placed at the first end 120'. The cutting device is in the first operating position shown in FIG. 10, i.e. with the actuator element 233 and handgrip 123 aligned, overlapped and oriented in the same direction with respect to the longitudinal extension axis 230a.

The surgical thread passes entirely through the passage channel 300 and emerges from the opening 130 at the second ends 120" and 230" of the guide body 120 and of cutting body 230 respectively.

The cutting device 100 is moved along the surgical thread so as to select the desired cutting length.

Figure 1:
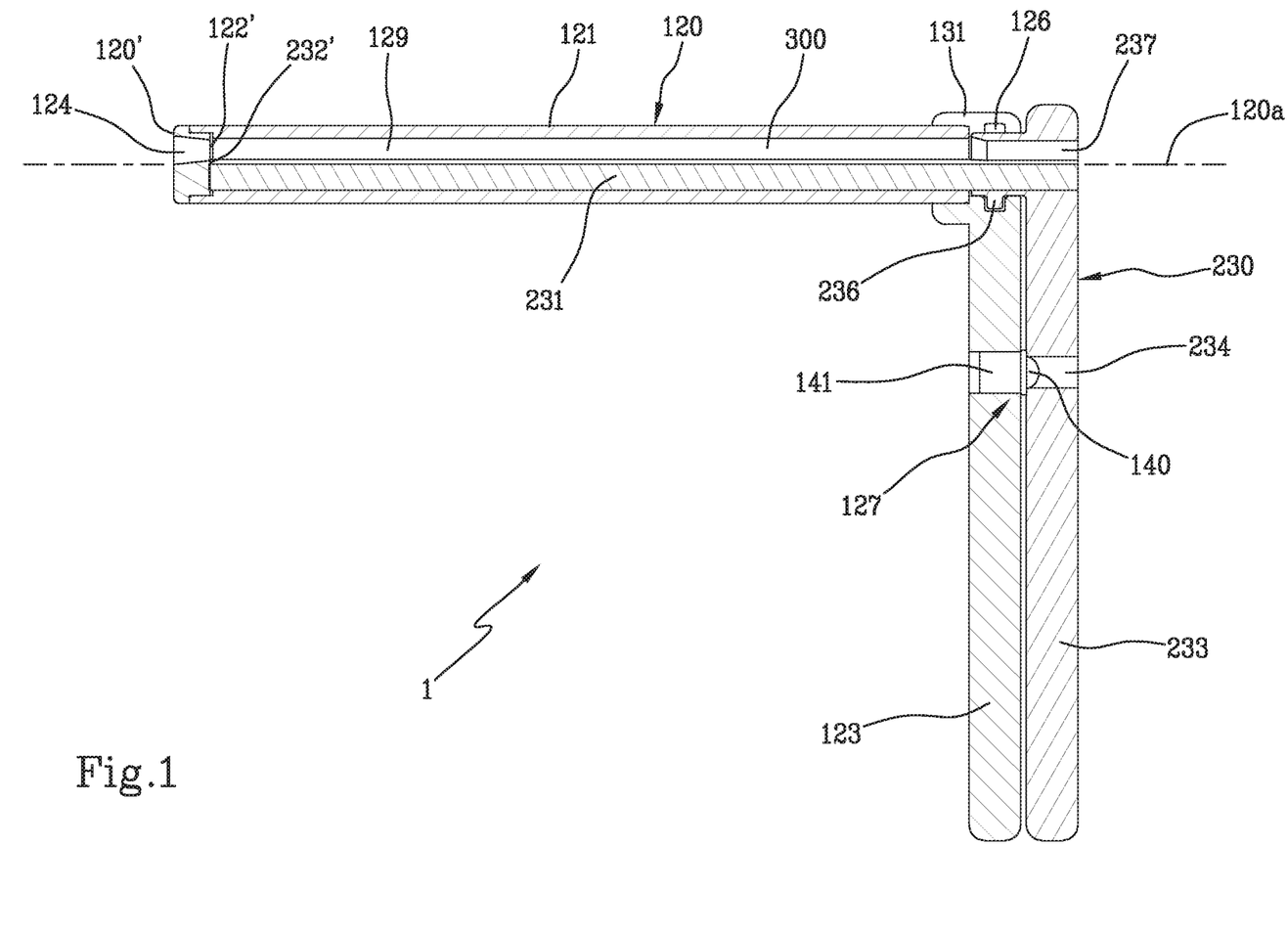
FIG. 1 shows a cutting device in accordance with the present invention in a sectioned configuration.
Figure 2:
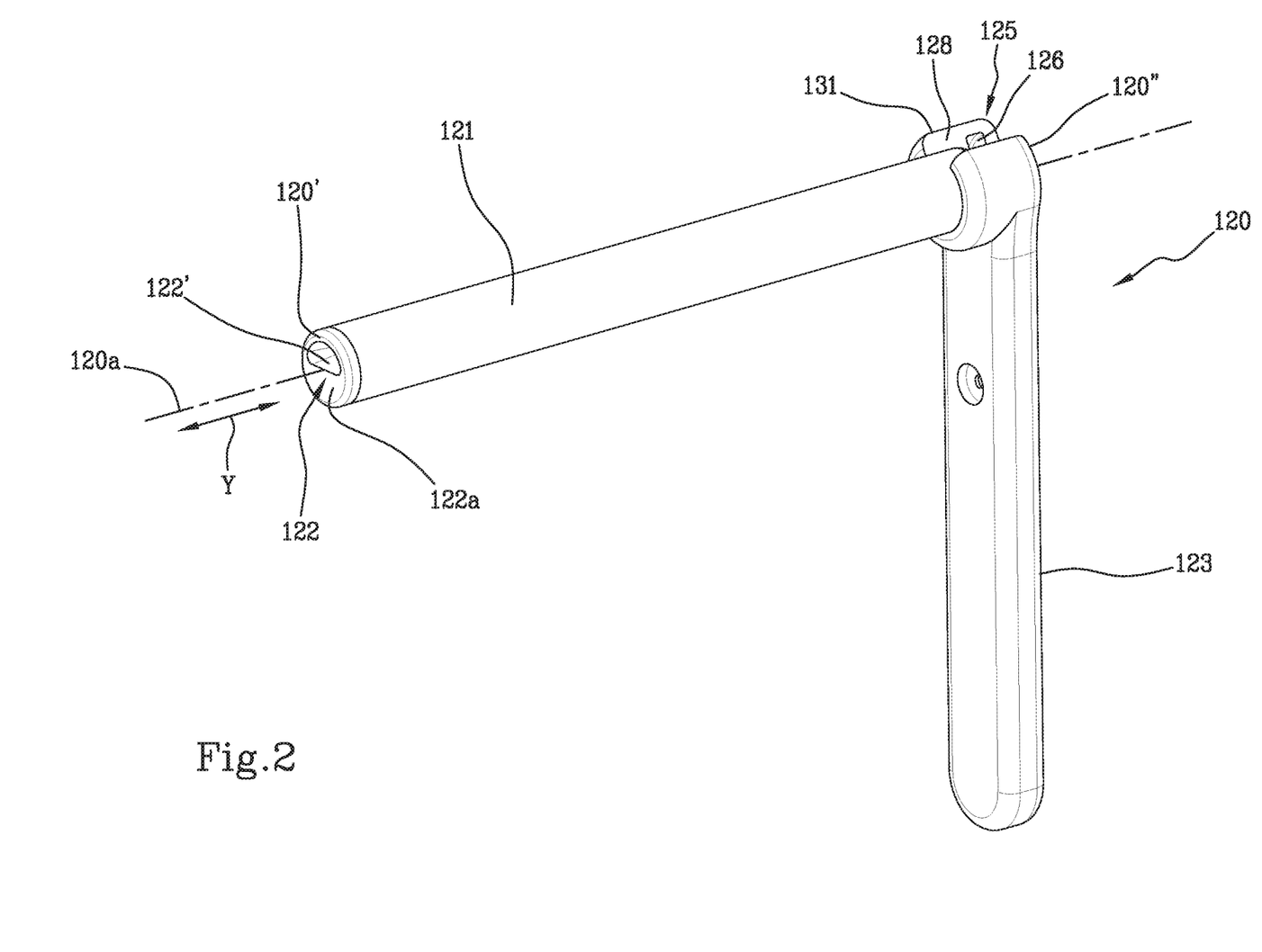
FIG. 2 is a front perspective view of a first portion of the cutting device that is the subject of the present invention.
Figure 3:
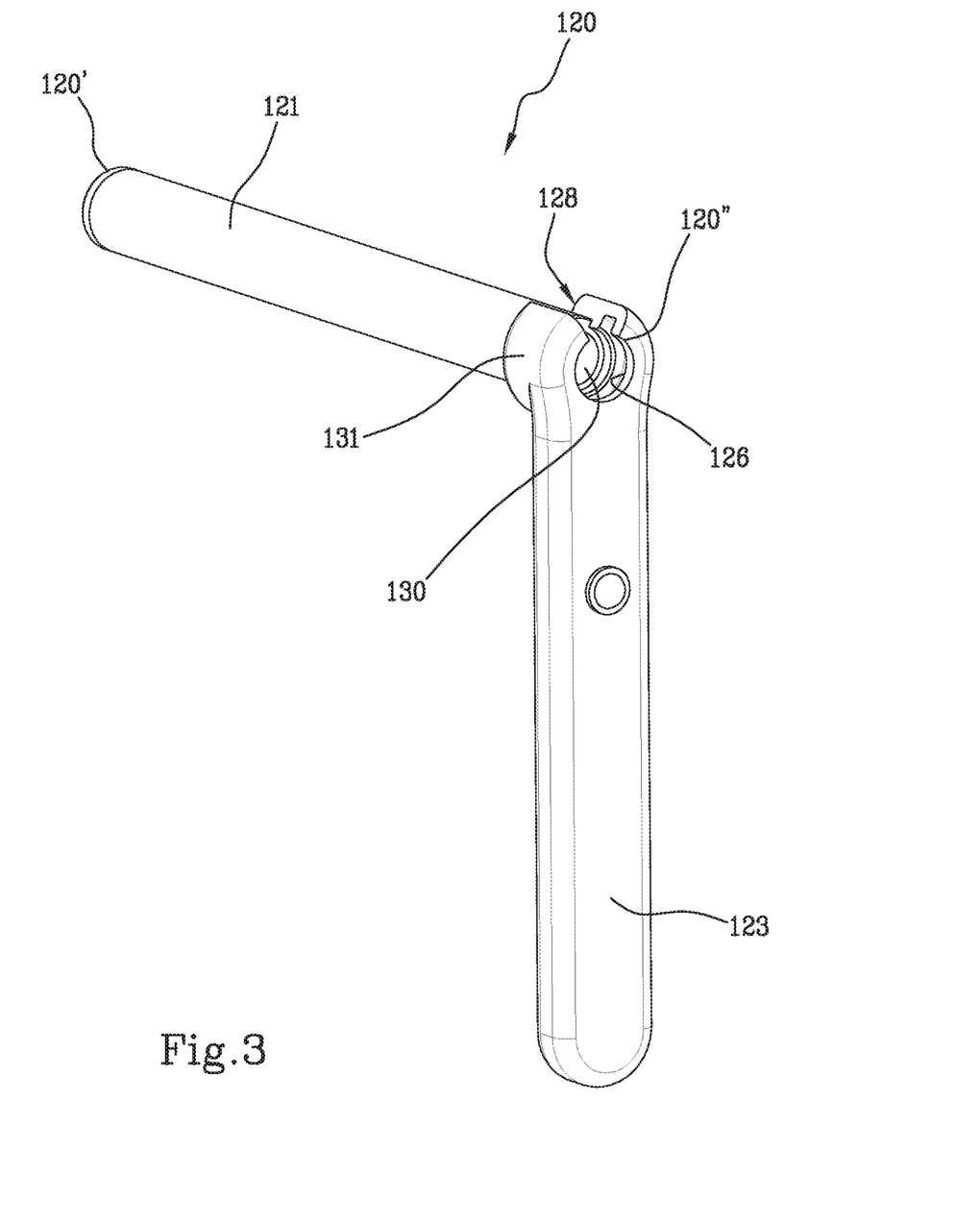
FIG. 3 is a rear perspective view of the first portion of the cutting device that is the subject of the present invention, shown in FIG. 2.
Figure 4:
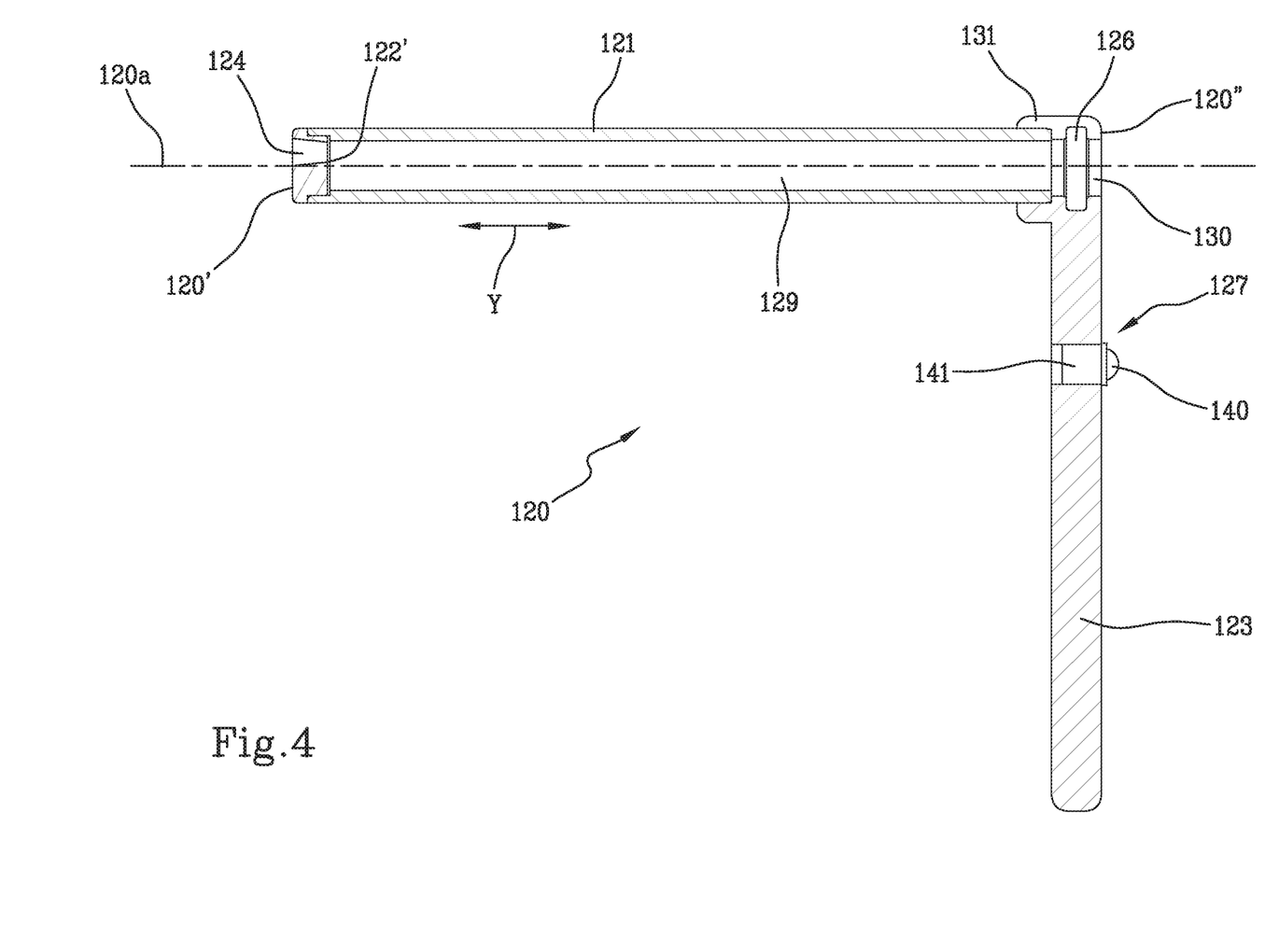
FIG. 4 is a side cross-sectional view of the first portion of the cutting device in FIGS. 2 and 3.
Figure 5:
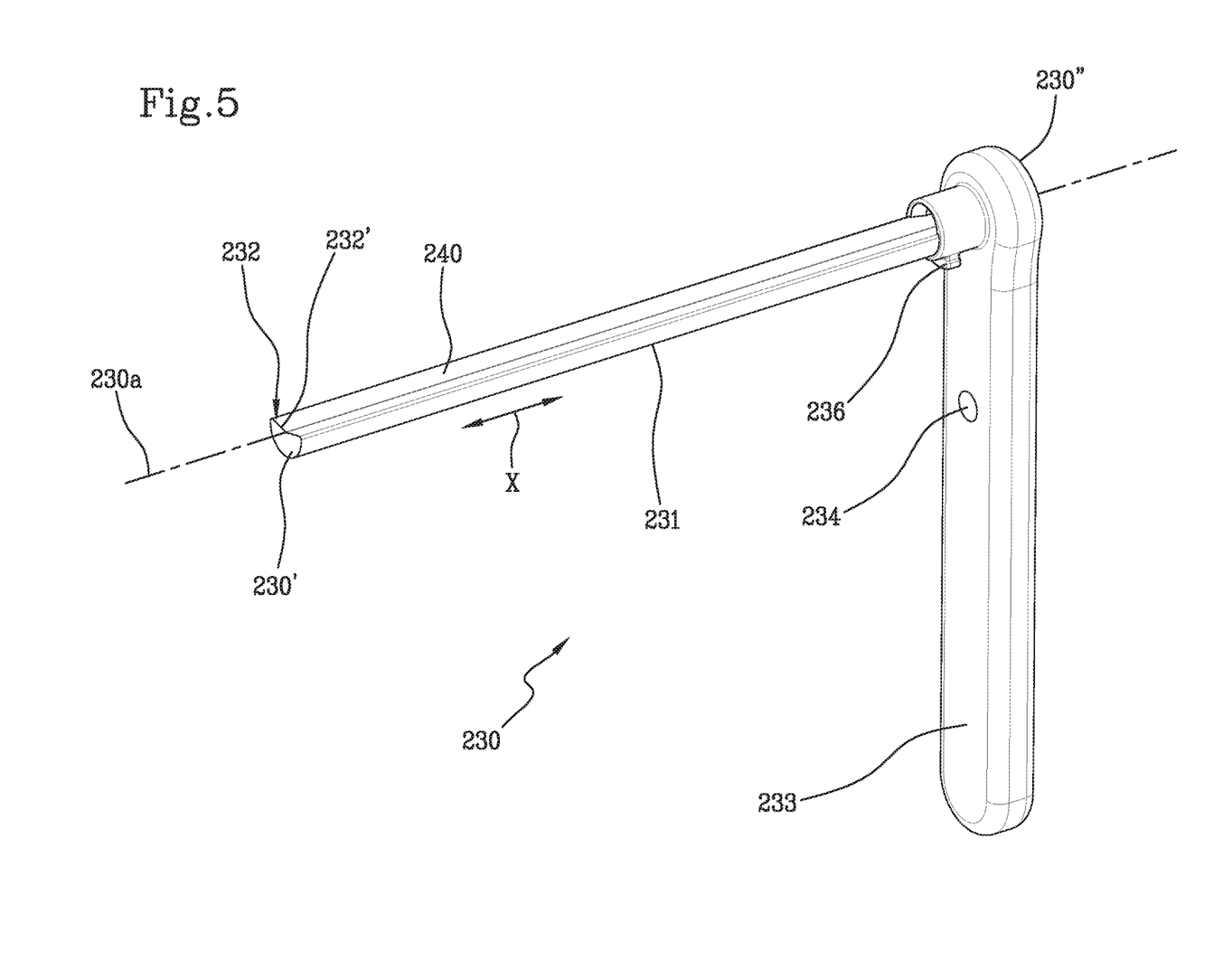
FIG. 5 is a front perspective view of a second portion of the cutting device that is the subject of the present invention.
Figure 6:
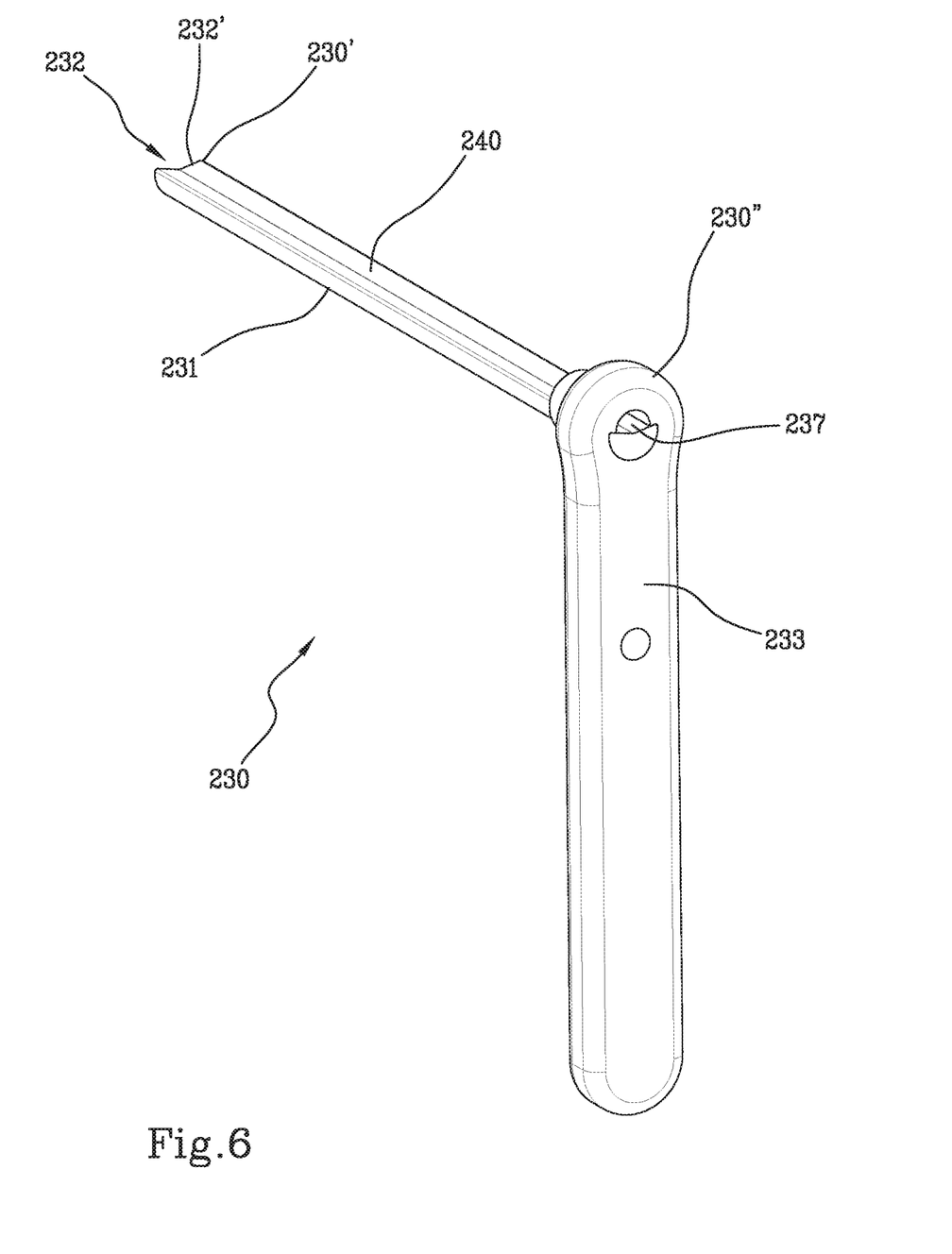
FIG. 6 is a rear perspective view of the second portion of the cutting device that is the subject of the present invention, shown in FIG. 5.
Figure 7:
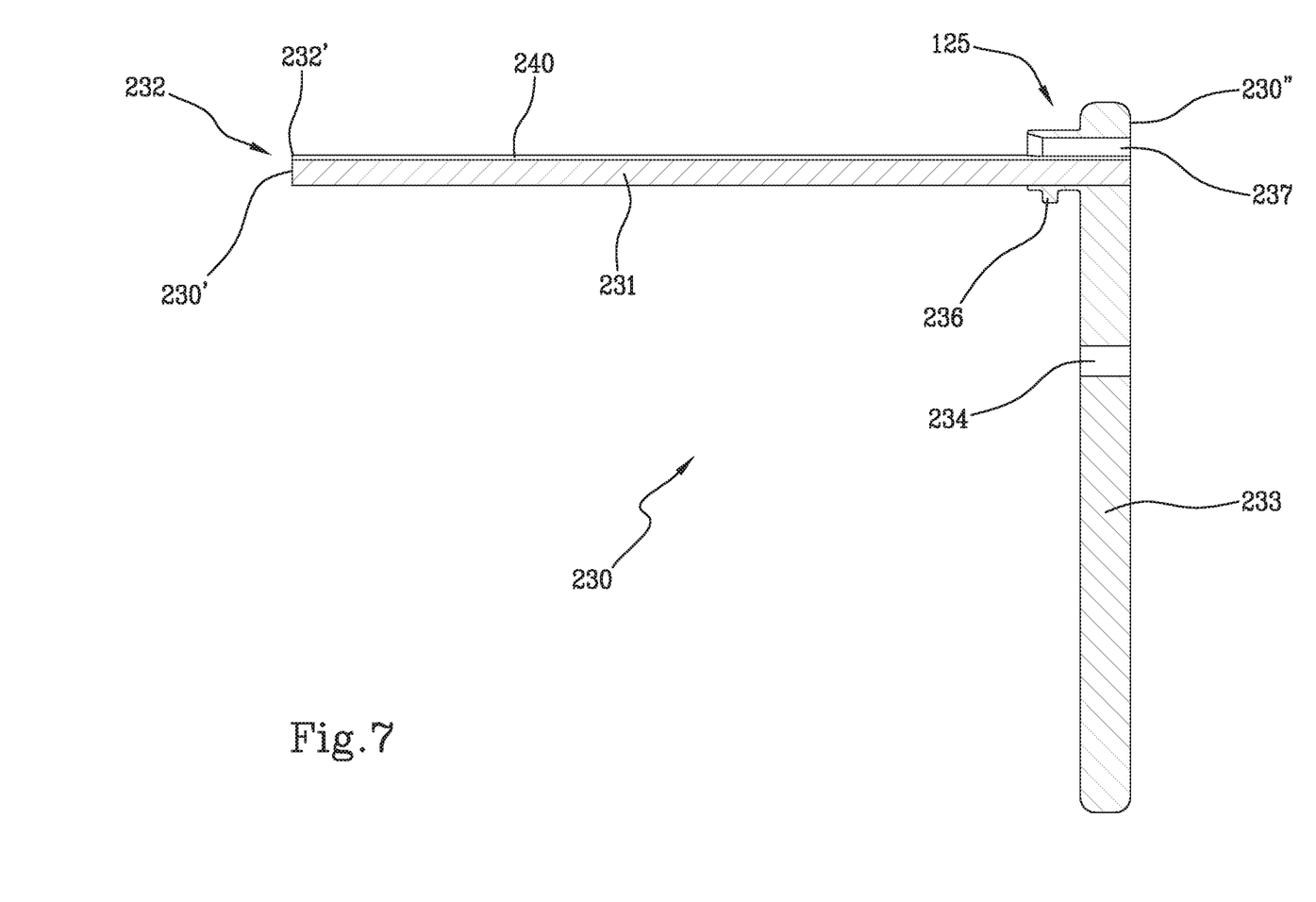
FIG. 7 is a side perspective view of the second portion of the cutting device in FIGS. 5 and 6.
Figure 8:
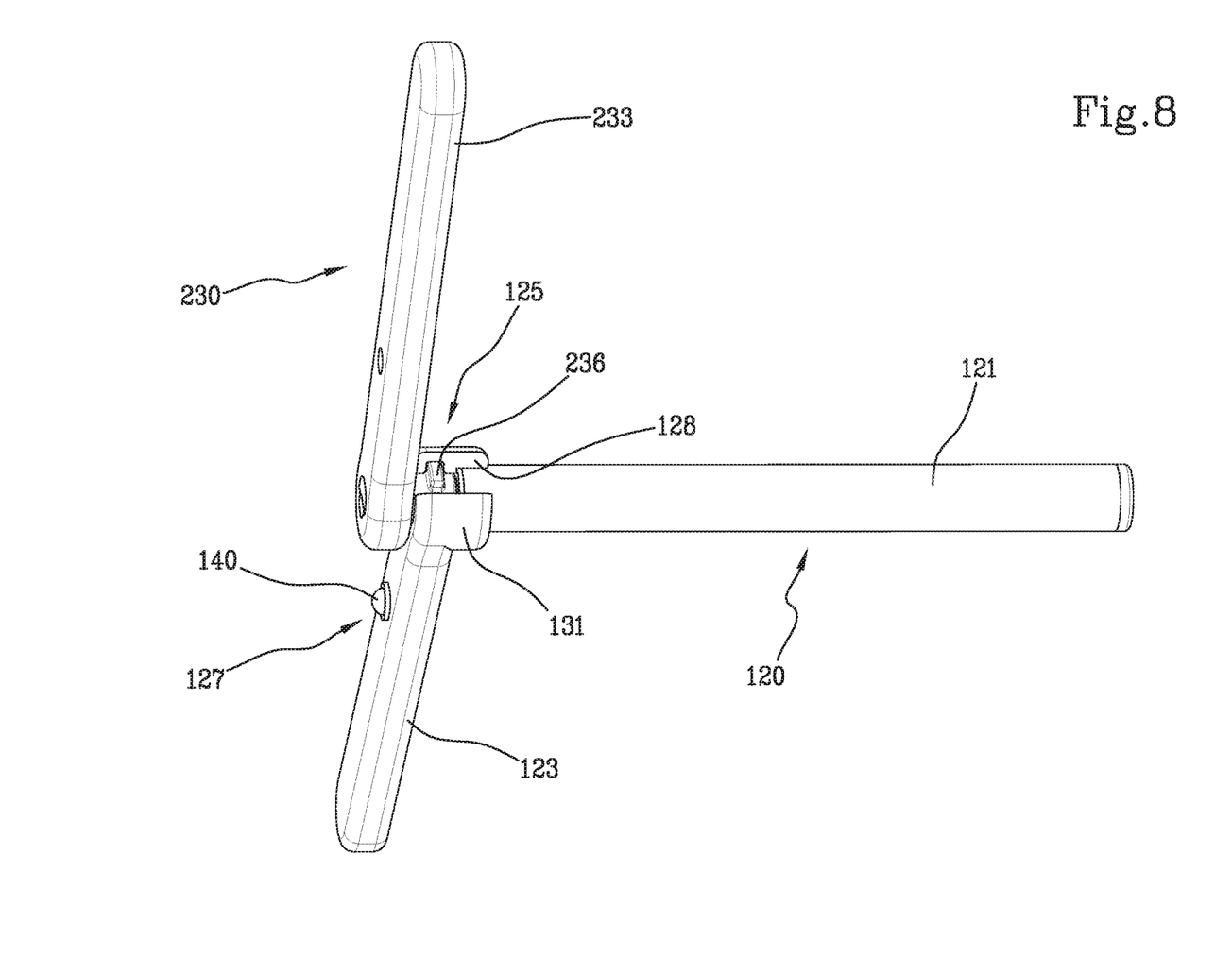
FIG. 8 shows an assembly step of the cutting device that is the subject of the present invention.

The actuator element 233 is then operated to move the cutting body 230 with respect to the guide body 120 from the first operating position (FIG. 10) to the second operating position (FIG. 8).

The relative movement between the cutting body 230 and the guide body 120 takes place by holding the latter in place by the handgrip 123, and by rotating the actuator element 233 with respect to the handgrip around the longitudinal axis 230a.

This rotation is transmitted to the abutment surface 232' of the second cutting zone 232 of the cutting body 230. This rotation determines the tangential intersection between the abutment surface 122' of the first cutting area 122 and the abutment surface 232' of the second cutting area 232, thus causing the thread to be cut as with scissor blades.

Once cut, the surgical thread remains inside the axial cavity 129 and the device can be removed from the patient's body.

This device allows considerable advantages to be obtained because it permits the cutting of the thread in total safety for the patient, avoiding the exposure and direct contact of the cutting elements with soft tissue or other parts of the patient.

The surgical thread remains inside the device, facilitating the removal operation and allowing the surgeon to handle the entire tool more easily at the surgical site.

The cutting device is very easy to use and allows a quick cut.

Contrary to what is known in the state of the art, the present invention does not have moving blades in contact with the patient's tissues. In fact, thanks to the particular shape of the guide body and the position of the two cutting areas, it is possible to cut the protruding thread from the knot without any possibility of contact between the patient's tissue and the blades.

Moreover, the particular shape of the guide body 21 and the central portion, as well as their particular reciprocal interaction, allow the surgeon to greatly limit the size of the necessary incision, obeying the dictates of minimally invasive surgery and, thus, allowing the patient a quick recovery and limiting the pain and discomfort to which he/she is subjected.

Additionally, the outer part of the guide body not only acts as a guide for the cutting operations, but also has the advantage of protecting the patient's tissue against the device's moving parts.

Surgeons particularly appreciate the presence of the through cavity during the pre-cut positioning steps of the tool near the knot. In fact, it will no longer be necessary for the surgeon to use the aid of touch to choose the position of the blades inside the surgical site, due to the presence of body fluids that limit the visibility of the blades.

With the present invention, instead, it will be sufficient to fit the cutting device on the surgical thread to be cut, by sliding the surgical thread protruding from the patient's body inside the through cavity to the desired position. Finally, it will be sufficient to perform the cut by simply rotating two bodies without exposed sharp parts and having rounded profiles, and to extract the cutting device from the patient's body.

From the above, it is clear that the cut thread remains trapped inside the cutting device, avoiding the need for the surgeon to maintain a firm grip on the ends of thread that are cut, as is, instead, required by the prior art. In fact, it is imperative that these ends of cut surgical thread be removed from inside the patient's body. Currently, this task is the responsibility of the surgeon or of one of his/her assistants who, while maintaining a firm grip on the ends protruding from the knot, removes them from the patient's body once the cut has been completed. It is easy to see how this operation can be annoying, since the surgical thread may be covered with body fluids that make it slippery and its removal, once cut, difficult.

The invention claimed is:

1. A cutting device for surgical threads comprising:
   a guide body having a tubular shape extending along a longitudinal axis, having an internal axial cavity defining a housing portion adapted to receive a surgical thread, said guide body comprising a first end, which is at least partially open to allow insertion of the surgical thread, a second end, and a first cutting area defined by an abutment surface of the guide body oriented transversely to the longitudinal axis of the guide body;
   a cutting body comprising:
      a central portion extending along a longitudinal axis and adapted to be inserted in said housing portion; said central portion having a section transverse to said longitudinal axis of said cutting body such as to define, when coupled in said housing portion, a passage channel, extending parallel to the longitudinal axis of said guide body, for housing said surgical thread;
      a first end equipped with a second cutting area defined by an abutment surface of the cutting body oriented transversely to the longitudinal axis of the cutting body; said second cutting area abutting against the first cutting area when said cutting body is at least partially received in the housing portion; said abutment surface of the cutting body having an angle comprised between 150° and 170° to define a housing zone for said surgical thread; and
      a second end; and
   an actuator element, capable of causing said cutting body to rotate relative to said guide body about said longitudinal extension axis of said cutting body between a first position, in which the abutment surfaces of said guide body and said cutting body, respectively, are arranged relative to each other so as to identify a passageway at the first ends of said housing portion and said second cutting area, respectively, communicating with said internal axial cavity, and a second position, in which said passageway is at least partially obstructed by the counter-rotating movement of said abutment surfaces, which intersect tangentially so as to cut the surgical thread therebetween;
   wherein the guide body has a coupling area adapted to provide an axially stable connection between the guide body and the cutting body; wherein said coupling area comprises an annular groove formed at the second end of said guide body, adapted to receive a corresponding radial projection provided at the second end of said cutting body, so as to allow mutual engagement, correct and stable relative axial positioning, and relative rotation between said cutting body and the guide body.

2. The cutting device for surgical threads according to claim 1, wherein the second end of the said guide body is axially opposite to the first end of the guide body and the second end having an opening for the exit of the surgical thread.

3. The cutting device for surgical threads according to claim 1, wherein the second end of the said cutting body is axially opposite to the first end of the cutting body and the second end having an opening for the exit of the surgical thread.

4. The cutting device for surgical threads according to claim 1, wherein said guide body has a gripping area to allow said guide body to be gripped.

5. The cutting device for surgical threads according to claim 4, wherein the actuator element has a cavity adapted to receive therein a locking element provided on the gripping area of the guide body, so that, when the locking element engages said cavity, the actuator element and the gripping area are aligned, forcing the guide body-and the cutting body in the first position.

6. The cutting device for surgical threads according to claim 5, wherein said locking element has an elastic abutment.

7. The cutting device for surgical threads according to claim 1, wherein said actuator element is connected to said cutting body.

8. The cutting device for surgical threads according to claim 1, wherein the guide body has a notch at the second end for inserting said projection in said groove.

9. The cutting device according to claim 1, wherein the first cutting area of the guide body has a substantially semi-cylindrical conformation with a base transverse to the longitudinal axis of the guide body, and the abutment surface of the guide body has an angle comprised between 150° and 180°.

10. The cutting device according to claim 1, wherein said cutting body has a substantially semi-circular cross-section.

11. A method of cutting a surgical thread by means of the cutting device as claimed in claim 1, comprising the steps of:
   a. Inserting a cutting body inside a guide body;
   b. Inserting the surgical thread inside the axial cavity of the guide body;
   c. Translating the cutting device along the surgical thread so as to select the desired cutting length;
   d. Operating the actuator element so as to move said cutting body relative to said guide body from the first position to the second position;
   e. Cutting the thread.

12. The method of cutting a surgical thread according to claim 11, wherein the step of operating the actuator element comprises the rotation of the actuator element relative to the gripping area, said rotation being transmitted to the second cutting area in order to cause intersection of the abutment surface of the guide body with the abutment surface of the cutting body.

* * * * *